United States Patent
Kim (10) Patent No.: US 10,578,540 B2
(45) Date of Patent: Mar. 3, 2020

(54) PARTICULATE MATTER SENSOR

(71) Applicants: Hyundai Motor Company, Seoul (KR); KIA Motors Corporation, Seoul (KR)

(72) Inventor: Dong Gu Kim, Gyeonggi-do (KR)

(73) Assignees: HYUNDAI MOTOR COMPANY, Seoul (KR); KIA MOTORS CORPORATION, Seoul (KR)

( * ) Notice: Subject to any disclaimer, the term of this patent is extended or adjusted under 35 U.S.C. 154(b) by 77 days.

(21) Appl. No.: 15/994,460

(22) Filed: May 31, 2018

(65) Prior Publication Data

US 2019/0195767 A1  Jun. 27, 2019

(30) Foreign Application Priority Data

Dec. 22, 2017  (KR) .................. 10-2017-0177709

(51) Int. Cl.
| | |
|---|---|
| *G01N 15/06* | (2006.01) |
| *F02D 41/14* | (2006.01) |
| *F01N 9/00* | (2006.01) |

(52) U.S. Cl.
CPC .......... *G01N 15/0656* (2013.01); *F01N 9/002* (2013.01); *F02D 41/1445* (2013.01); *F02D 41/1446* (2013.01); *F02D 41/1494* (2013.01); *F01N 2560/05* (2013.01); *F01N 2560/20* (2013.01)

(58) Field of Classification Search
CPC .............. G01N 15/06; G01N 15/0656; G01N 2015/0046; G01N 15/10; G01N 15/1031; F02D 41/1438; F02D 41/1445; F02D 41/1446; F02D 41/1493; F01N 2560/05
USPC ............ 73/23.2, 28.01, 31.03, 31.05, 114.69
See application file for complete search history.

(56) References Cited

U.S. PATENT DOCUMENTS

| | | | | |
|---|---|---|---|---|
| 3,349,619 | A * | 10/1967 | Millar ...................... | G01F 1/40 73/861.52 |
| 5,008,628 | A * | 4/1991 | Krigmont ............ | G01N 27/043 324/464 |
| 6,972,080 | B1 * | 12/2005 | Tomioka ................ | C12M 47/02 204/450 |
| 2008/0134753 | A1 * | 6/2008 | Jun ...................... | G01N 27/128 73/23.2 |
| 2009/0051376 | A1 | 2/2009 | Schnell et al. | |

(Continued)

*Primary Examiner* — Benjamin R Schmitt
(74) *Attorney, Agent, or Firm* — Brinks Gilson & Lione (57) ABSTRACT

Disclosed is a particulate matter sensor having a structure which may achieve a reduction in distance between two electrodes and an increase in area of measurement electrodes so as to facilitate enhancement in measurement accuracy, reliability, and sensitivity, and reduce influence on sensitivity according to sensor mounting directions. The particulate matter sensor may include a housing provided with an inlet and an outlet, and a sensing unit installed within the housing so as to pass exhaust gas, the sensing unit may include a laminate including an electrically insulating substrate, a first electrode provided on one surface of the electrically insulating substrate, a second electrode provided on the other surface of the electrically insulating substrate, and a porous layer stacked on one of the first electrode and the second electrode and having a structure to pass the exhaust gas, and the laminate is spirally wound on a base unit.

9 Claims, 4 Drawing Sheets

(56) References Cited

U.S. PATENT DOCUMENTS

2012/0324982 A1 12/2012 Hocken et al.
2013/0298640 A1 11/2013 Ante et al.

* cited by examiner

FIG. 1

EXHAUST GAS FLOW

FIG. 2

- - -> : EXHAUST GAS FLOW

PARTICULATE MATTER SENSOR

CROSS-REFERENCE TO RELATED APPLICATION

This application claims priority to and the benefit of priority to Korean Patent Application No. 10-2017-0177709, filed on Dec. 22, 2017, the entire contents of which are incorporated herein by reference.

FIELD

The present disclosure relates to a particulate matter sensor.

BACKGROUND

The statements in the section merely provide background information related to the present disclosure and may not constitute prior art.

Recently, as exhaust gas regulations have been further tightened, after-treatment devices to purify exhaust gas have been developed.

Particularly, regulations on particulate matter (PM), such as soot, etc., and nitrogen oxide ($NO_x$) contained in exhaust gas of diesel vehicles are being further tightened.

As after-treatment technology which reduces particulate matter and is close to commercialization, a diesel particulate filter (DPF) may be used and a particulate matter (PM) sensor may be installed at the rear end of the DPF.

In general, the particulate matter (PM) sensor is used to sense an amount of particulate matter collected by the DPF or to diagnose whether or not an exhaust gas reduction device (an after-treatment device) fails.

Recently, On-Board Diagnostic (OBD) regulations require not only satisfaction of tightened exhaust gas regulations but also diagnostic ability to sense failure and degradation degree of degradation of parts related to exhaust gas and satisfaction of various rules related to standardization in a customer service market.

In order to cope with Euro 6 (EU emission standards) diesel regulations, the particulate matter (PM) sensor may be used to measure a level of particulate matter which is not filtered out by the DPF and is exhausted to the outside.

Further, an electronic control unit (ECU) diagnoses whether or not the DPF fails through a measured value of the particulate matter (PM) sensor and informs driver of failure of the DPF so as to have the car serviced.

Particulate matter (PM) sensors are generally divided into an accumulation type and a real-time type. An accumulation type particulate matter (PM) sensor senses current change between two electrodes according accumulation of particulate matter on the electrodes, to which voltage is applied.

For accumulation type, which is a type directed to detecting change in resistance or capacitance in a sensing unit generated due to accumulation of particulate matter included in the exhaust gas, a resistive type and a capacitive type are known.

A capacitive type particulate matter (PM) sensor includes a plurality of first electrodes disposed in parallel on the surface of the sensor and a plurality of second electrodes disposed at a designated distance from the first electrodes, and measures capacitance between the first electrodes and the second electrodes using the area of particulate matter accumulated between the first electrodes and the distance between the first electrodes and the second electrodes, thus easily detecting particulate matter which is not filtered out by a diesel particulate filter and is discharged downstream.

In a resistive type particulate matter (PM) sensor, when particulate matter is accumulated under the condition that bias voltage is applied between two electrodes, signal change between the two electrodes due to an accumulation amount of the particulate matter occurs (i.e., resistance is reduced) and, in this case, the resistive type particulate matter (PM) sensor diagnoses whether or not a diesel particulate filter fails by comparing a measured value with a set value (comparing the particulate matter generated amount with a set amount).

Such a particulate matter (PM) sensor removes particulate matter by driving a heater, if the particulate matter (PM) sensor judges that the diesel particulate filter is normally operated, (sensor regeneration) and then measures current change (i.e., resistance change) corresponding to an amount of particulate matter accumulated between the electrodes (i.e., repeats a cycle of sensor regeneration and measurement).

As prior art documents, U.S. Patent Publication No. US 2013/0298640 discloses a method for operating a soot sensor. In a disclosed particulate matter sensor, electrodes are formed only on one surface of a substrate and thus sensitivity is low, and sensitivity is influenced by a sensor mounting direction.

Further, U.S. Patent Publication No. US 2012/0324982 and U.S. Patent Publication No. US 2009/0051376 disclose application of a mask process and a laser electrode patterning process to reduce a distance between two electrodes so as to improve sensitivity.

However, we have discovered that the mask process has a limit in reducing the distance between electrodes and may cause short circuit between the two electrodes after sintering.

Further, we have found that the laser electrode patterning process may relatively reduce the distance between electrodes but may result in a cost increase and reduction in ease of mass production.

SUMMARY

The present disclosure provides a particulate matter sensor having an improved structure which may achieve a reduction in distance between two electrodes and an increase in area of measurement electrodes so as to facilitate enhancement in measurement accuracy, reliability, and sensitivity, and reduce influence on sensitivity according to sensor mounting directions.

In one aspect, the present disclosure provides a particulate matter sensor including a housing provided with an inlet and an outlet so that exhaust gas introduced into the housing through the inlet passes through an inner space of the housing and is then discharged to the outside of the housing through the outlet, and a sensing unit installed within the inner space of the housing so as to pass the exhaust gas, wherein the sensing unit includes a laminate including an electrically insulating substrate, a first electrode provided on one surface of the electrically insulating substrate, a second electrode provided on the other surface of the electrically insulating substrate, and a porous layer stacked on one of the first electrode and the second electrode and having a structure to pass the exhaust gas, and the laminate is spirally wound on a base unit.

Other aspects and forms of the present disclosure are discussed below.

Further areas of applicability will become apparent from the description provided herein. It should be understood that the description and specific examples are intended for purposes of illustration only and are not intended to limit the scope of the present disclosure.

DRAWINGS

In order that the disclosure may be well understood, there will now be described various forms thereof, given by way of example, reference being made to the accompanying drawings, in which.

The above and other features of the present disclosure will now be described in detail with reference to certain exemplary embodiments thereof illustrated in the accompanying drawings which are given hereinbelow by way of illustration only, and thus are not limitative of the present disclosure, and wherein.

It should be understood that the appended drawings are not necessarily to scale, presenting a somewhat simplified representation of various features illustrative of the basic principles of the present disclosure. The specific design features of the present disclosure as disclosed herein, including, for example, specific dimensions, orientations, locations, and shapes will be determined in part by the particular intended application and use environment.

In the figures, reference numbers refer to the same or equivalent parts of the present disclosure throughout the several figures of the drawing.

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features.

Hereinafter reference will now be made in detail to various forms of the present disclosure, examples of which are illustrated in the accompanying drawings and described below. While the present disclosure will include description of exemplary forms, it will be understood that the present description is not intended to be limited to the exemplary forms. On the contrary, the present disclosure is intended to cover not only the exemplary form, but also various alternatives, modifications, equivalents and other variations within the spirit and scope of the present disclosure as defined by the appended claims.

In the following description of the forms of the present disclosure, the term "including" will be interpreted as indicating presence of characteristics, numbers, steps, operations, elements and parts stated in the specification or combinations thereof, and do not exclude the presence of one or more other characteristics, numbers, steps, operations elements or combinations thereof, or possibility of adding the same.

The present disclosure provides a particulate matter sensor having an improved structure which may achieve reduction in a distance between two electrodes and increase in the area of measurement electrodes so as to facilitate enhancement in measurement accuracy, reliability, and sensitivity, and reduce influence on sensitivity according to sensor mounting directions.

For this purpose, a particulate matter sensor in which a sensing unit including electrodes has an improved configuration is disclosed.

The particulate matter sensor in accordance with the present disclosure includes the sensing unit having technical characteristics and may thus employ a capacitive type or resistive type particulate matter sensor including the sensing unit.

That is, in addition to the sensing unit, which will be described later, a known circuit configuration connected to the electrodes of the sensing unit may be additionally provided, thus forming a capacitive type particulate matter sensor or a resistive type particulate matter sensor.

Figure 1:
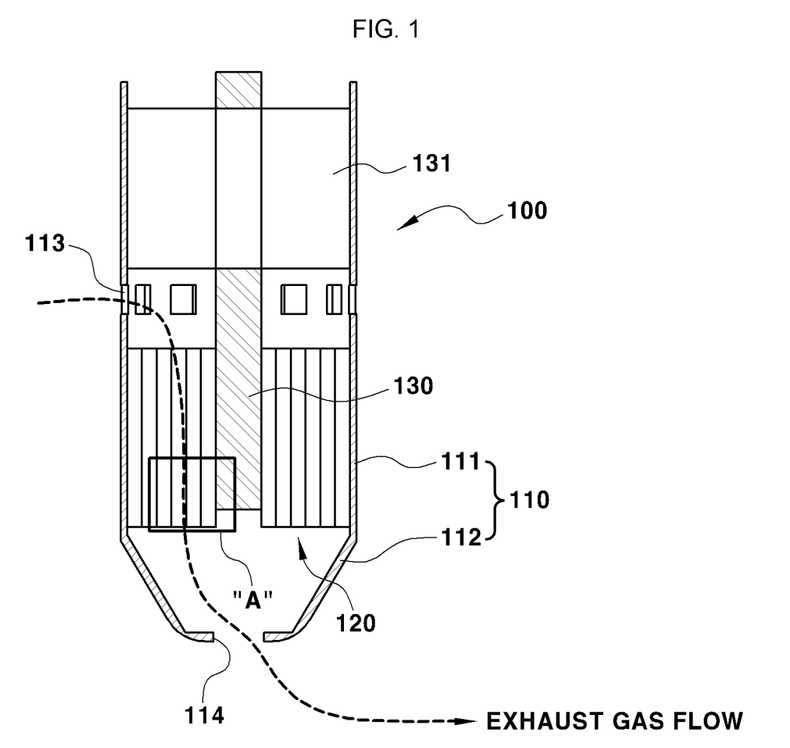
FIG. 1 is a longitudinal-sectional view illustrating a particulate matter sensor in accordance with one form of the present disclosure.
Figure 2:
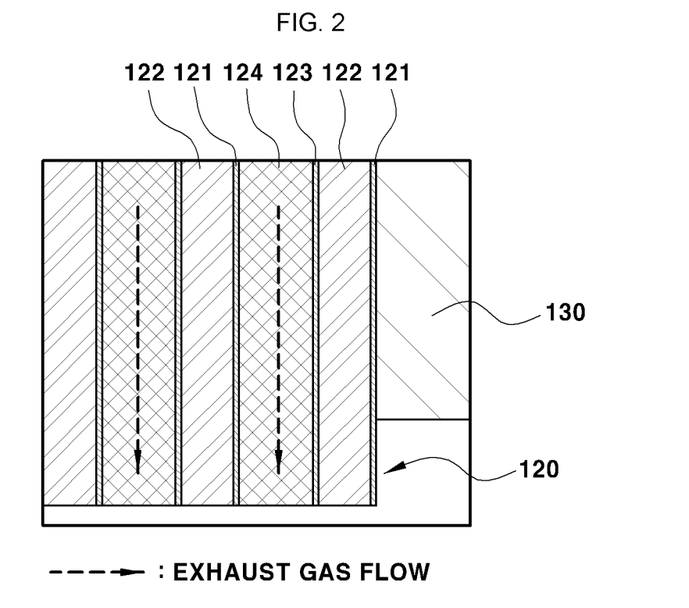
FIG. 2 is an enlarged view illustrating the configuration of a sensing unit and exhaust gas flow paths of the particulate matter sensor in accordance with the form of the present disclosure.

FIG. 1 is a longitudinal-sectional view illustrating a particulate matter sensor in accordance with one form of the present disclosure, and FIG. 2 is an enlarged view illustrating the configuration of a sensing unit and exhaust gas flow paths of the particulate matter sensor in accordance with the form of the present disclosure.

Figure 3:
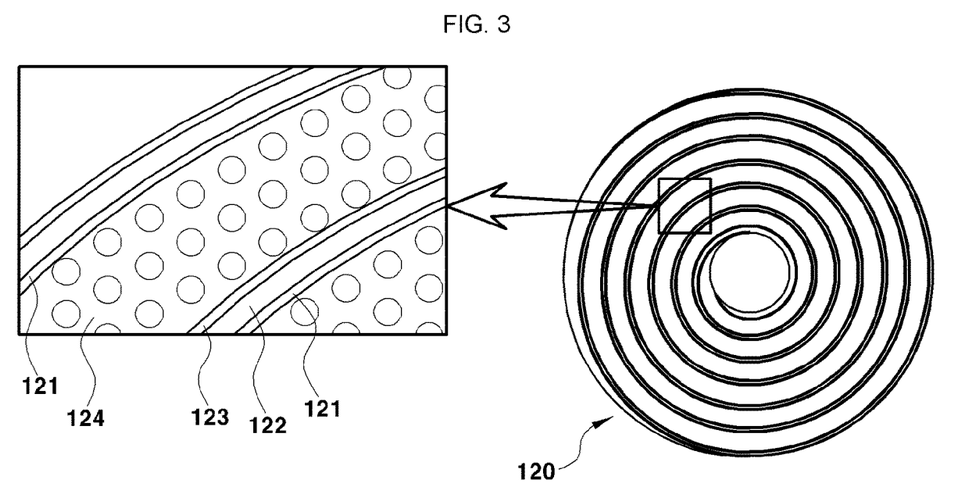
FIG. 3 is a cross-sectional view of the sensing unit of the particulate matter sensor in accordance with the form of the present disclosure and an enlarged view of a specific region of the sensing unit, respectively.
Figure 4:
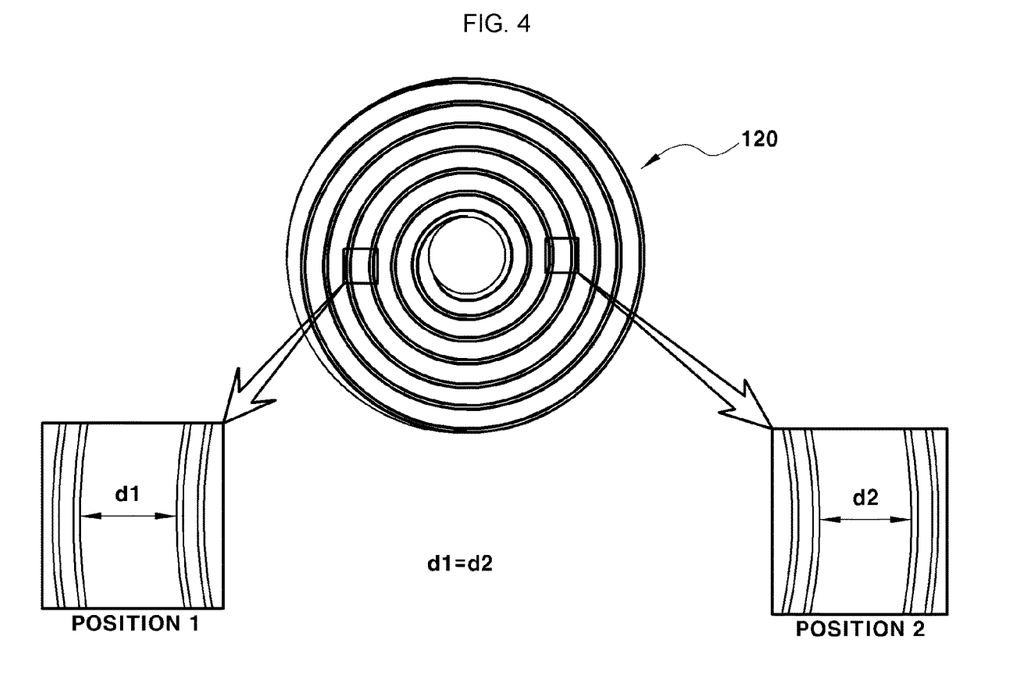
FIG. 4 is a cross-sectional view of the sensing unit of the particulate matter sensor in accordance with the form of the present disclosure and enlarged views of specific regions of the sensing unit.

FIG. 3 is a cross-sectional view of the sensing unit of the particulate matter sensor in accordance with the form of the present disclosure and an enlarged view of a specific region of the sensing unit, and FIG. 4 is a cross-sectional view of the sensing unit of the particulate matter sensor in accordance with the form of the present disclosure and enlarged views of specific regions of the sensing unit.

As exemplarily shown in FIGS. 1 to 4, a particulate matter sensor 100 in accordance with one form of the present disclosure includes a housing 110 provided with an inlet 113 and an outlet 114 so that exhaust gas passes through the inner space of the housing 110 through the inlet 113 and the outlet 114, and a cylindrical sensing unit 120 installed within the housing 110 so as to pass the exhaust gas.

Here, the housing 110 may be manufactured to have a cylindrical container shape, the inlet 113 through which exhaust gas is introduced into the housing 110 is formed at one side of the housing 110, and the outlet 114 through which the exhaust gas is discharged to the outside of the housing 110 is formed at the other side of the housing 110.

As exemplarily shown in FIG. 1, the inlet 113 may be located at an upper portion of the housing 110, and the outlet 114 may be located at a lower portion of the housing 110.

The sensing unit 120 is located between the inlet 113 and the outlet 114 within the housing 110, and exhaust gas introduced into the housing 110 through the inlet 113 passes through the sensing unit 120 and is then discharged to the outside of the housing 110 through the outlet 114.

In more detail, after exhaust gas is introduced into the housing 110 through the inlet 113 formed at the upper portion of the housing 110, the exhaust gas may pass through a porous layer 124 of the sensing unit 120, which will be described later, in the downward direction within the housing 110, as exemplarily shown in FIG. 2, and the exhaust gas passed through the porous layer 124 may be discharged to the outside of the housing 110 through the outlet 114 formed at the lower portion of the housing (with reference to FIG. 2).

In the present disclosure, the porous layer 124 of the sensing unit 120 is interposed between a first electrode 121 and a second electrode 123 and, while exhaust gas passes through the porous layer 124, particulate matter included in the exhaust gas is collected and accumulated in the porous layer 124.

In this form, the inlet 113 through which exhaust gas is introduced into the housing 110 may be formed at a side surface portion (i.e., a cylindrical part 111) of the housing 110, and the inlet 113 may include a plurality of holes arranged at the side surface portion (i.e., the cylindrical part 111) of the housing 110 at designated intervals in the circumferential direction (with reference to FIG. 1).

Further, a diameter reduction part 112 having a conical shape, the diameter of which is gradually reduced, is formed integrally with one axial side of the cylindrical part 111 of the housing 110, and the outlet 114 through which the exhaust gas is discharged to the outside is formed through a front end of the conical diameter reduction part 112.

Further, the sensing unit 120 is disposed in the housing 110 so as to be located at the upstream region of the diameter reduction part 112, and exhaust gas introduced into the housing 110 through the inlet 113 passes through the sensing unit 120 and is then discharged to the outside of the housing 110 through the outlet 114 of the diameter reduction part 112.

In the present disclosure, the sensing unit 120 includes a laminate including an electrically insulating substrate 122, the first electrode 121 provided on one surface of the electrically insulating substrate 122, the second electrode 123 provided on the other surface of the electrically insulating substrate 122, and the porous layer 124 stacked on one of the first electrode 121 and the second electrode 123 and having a structure which may pass exhaust gas.

Here, the laminate of the sensing unit 120 is spirally wound on a base unit 130.

Hereinafter, the configuration of such a sensing unit 120 will be described in more detail.

First, the sensing unit 120 includes the two electrodes 121 and 123 disposed at a designated distance, and the porous layer 124 disposed between the two electrodes 121 and 123 and having a porous structure, through which exhaust gas may pass.

In the sensing unit 120 of the particulate matter sensor 100 in accordance with this form of the present disclosure, as exemplarily shown in FIGS. 2 to 3, the electrically insulating substrate 122 is disposed between one surface of the first electrode 121 and one surface of the second electrode 123, and the porous layer 124 is disposed between the other surface of the second electrode 123 and the other surface of the first electrode 121.

That is, since the sensing unit 120 is a kind of spirally wound laminate, the sensing unit 120 has a configuration in which the first electrode 121, the substrate 122, the second electrode 123, the porous layer 124, the first electrode 121, the substrate 122, the second electrode 123, and the porous layer 124 are repeatedly stacked on the base unit 130 in the outward direction.

In this form, the sensing unit 120 may have a circular cross-section (have a cylindrical shape except for the central base unit 130) so as to be received and located within the cylindrical part 111 of the housing 110, and be installed such that the outer circumferential surface of the sensing unit 120 contacts the inner circumferential surface of the cylindrical part 111 of the housing 110.

Further, the sensing unit 120 is installed so as to be located between the downstream region of the inlet 113 and the upstream region of the outlet 114 within the housing 110 and, thus, exhaust gas introduced into the housing 110 through the inlet 113 passes through the porous layer 124 of the sensing unit 120 and is then discharged to the outside of the housing 110 through the outlet 114.

Consequently, while exhaust gas passes through the porous layer 124, particulate matter PM included in the exhaust gas is accumulated in the porous layer 124, and the amount of the particulate matter PM accumulated in the porous layer 124 may be measured by reading an electrical signal according to the amount of the accumulated particulate matter PM through the electrodes 121 and 123.

The sensing unit 120 may be combined with an end of the base unit 130 within the housing 110, and the base unit 130 may be provided as a long rod member having a circular cross-section and be installed so as to be extended in the axial direction within the housing 110.

Here, the base unit 130 may be fixed to and supported by a support 131 separately installed within the housing 110.

The base unit 130 may be installed so as to pass through the center of the sensing unit 120 within the housing 110. Here, the sensing unit 120 is configured so as to be combined with the outer circumferential surface of the end of the base unit 130.

Thereby, as exemplarily shown in FIG. 3, when viewing the cross-section of the sensing unit 120, the sensing unit 120 is disposed around the base unit 130, the base unit 130 is located at the center of the sensing unit 120, and the sensing unit 120 has a circular cross-section under the condition that the base unit 130 and the sensing unit 120 are combined with each other.

Of course, the overall shape of the sensing unit 120 except for the base unit 130 is a cylindrical shape having a hollow formed at the center thereof so that the base unit 130 is inserted into the hollow.

In more detail, the sensing unit 120 includes the substrate 122 formed of an insulating material, the first and second electrodes 121 and 123 stacked on both surfaces of the substrate 122, and the porous layer 124 stacked on the second electrode 123.

Here, the sensing unit 120 has a structure, as described above, in which the first electrode 121 is stacked on one surface of the porous layer 124, the second electrode 123 is stacked on the other surface of the porous layer 124, and the first electrode 121, the substrate 122, the second electrode 123 and the porous layer 124 are spirally wound on the base unit 130.

Hereinafter, a structure formed by sequentially stacking the first electrode 121, the substrate 122, the second electrode 123 and the porous layer 124 will be referred to as a laminate.

In the present disclosure, the sensing unit 120 may be formed by spirally winding the laminate on the outer circumferential surface of the base unit 130 such that the first electrode 121 serves as the innermost layer bonded to the outer circumferential surface of the base unit 130.

The laminate has a structure in which the first electrode 121 and the second electrode 123 are located on both surfaces of the substrate 122 and the porous layer 124 is stacked on the second electrode 123 and, as exemplarily shown in FIG. 3, when the laminate is spirally wound on the base unit 130 such that the first electrode 121 surrounds the outer circumferential surface of the base unit 130, one surface of the porous layer 124 is stacked on and bonded to the second electrode 123 and the other surface of the porous layer 124 is stacked on and bonded to the first electrode 121.

That is, as exemplarily shown in FIG. 3, if the laminate, in which one surface of the porous layer 124 is stacked on the second electrode 123, is repeatedly wound on the base unit 130 so that the other surface of the porous layer 124 is stacked on the first electrode 121, the first electrode 121 and the second electrode 123 become disposed on both surfaces of the porous layer 124, and such a structure means that the porous layer 124 is interposed between the first electrode 121 and the second electrode 123.

The surface of the porous layer 124 on which the second electrode 123 is stacked and bonded may be an inner surface of the porous layer 124 when viewing the cross-section of FIG. 3.

Further, while the laminate is repeatedly spirally wound on the base unit 130, the first electrode 121 is stacked and bonded on the surface of the porous layer 124 and such a surface of the porous layer 124 on which the first electrode 121 is continuously stacked and bonded may be an outer surface of the porous layer 124 when viewing the cross-section of FIG. 3.

As such, the laminate is spirally wound on the base unit 130 so as to have a structure in which the first electrode 121, the substrate 122, the second electrode 123, the porous layer 124, the first electrode 121, the substrate 122, the second electrode 123, and the porous layer 124 are repeatedly stacked on the base unit 130 in the outward direction from the base unit 130. In such a structure of the sensing unit 120, a distance between the two electrodes 121 and 123 may be adjusted by controlling the thickness of the porous layer 124.

With reference to FIG. 3, it may be confirmed that the thickness of the porous layer 124 interposed between the first electrode 121 and the second electrode 123 corresponds to the distance between the first electrode 121 and the second electrode 123.

In this form of the present disclosure, as exemplarily shown in FIG. 4, the distance between the two electrodes 121 and 123 related to sensor sensitivity is uniform at all positions. Here, the distance between the two electrodes 121 and 123 is determined by the thickness of the porous layer 124.

In this form of the present disclosure, the thickness of the porous layer 124 interposed between the first electrode 121 and the second electrode 123, i.e., the distance between the first electrode 121 and the second electrode 123, may be 20-50 μm.

If the distance between the first electrode 121 and the second electrode 123 is less than 20 μm, difficulty in thickness reproducibility of the porous layer 124 is caused and, if the distance between the first electrode 121 and the second electrode 123 exceeds 50 μm, the distance between the first electrode 121 and the second electrode 123 is excessively increased and sensitivity may become lower than a desired level of the sensor 100.

In addition to the thickness of the porous layer 124, an axial length of the sensing unit 120 (a length of the cylindrical-shaped sensing unit 120), a diameter of the sensing unit 120, etc. are related to sensitivity of the sensor 100.

Sensitivity of the sensor 100 may be increased as the thickness of the porous layer 124 is decreased and the distance between the first electrode 121 and the second electrode 123 is decreased, and sensitivity of the sensor 100 may be increased as the axial length and diameter of the sensing unit 120 are increased.

Conventionally, a distance between two electrodes may become 20 μm using a complicated and expensive process, such as electrode patterning using a laser, but such a process may be accompanied by, for example, cost increase and reduction in ease of mass production.

On the other hand, if the sensing unit 120 is formed by spirally winding the laminate on the base unit 130, as described above, a distance between two electrodes may be easily reduced and a contact area between a part in which particulate matter is accumulated and the electrodes may be greatly increased.

Further, a manufacturing process may be simplified, the sensing unit 120 having a wide electrode area may be manufactured using simple equipment and, thus, cost reduction and improvement in ease of mass production may be achieved.

Moreover, the sensing unit 120 provided as the laminate is manufactured to form a cylindrical shape around the base unit 130 and, thus, influence of a sensor mounting direction on sensor sensitivity may be removed.

In this form of the present disclosure, the substrate 122 provided with both surfaces, on which the first electrode 121 and the second electrode 123 are stacked, is formed of an electrically insulating material and, for example, a ceramic sheet having a predetermined thickness may be used as the substrate 122.

Here, the substrate 122 may have a thickness of 100-200 μm.

The electrodes 121 and 123 may be formed of a conductor having electrical conductivity and, for example, be formed of a general electrode material which is known in the art.

Figure 5:
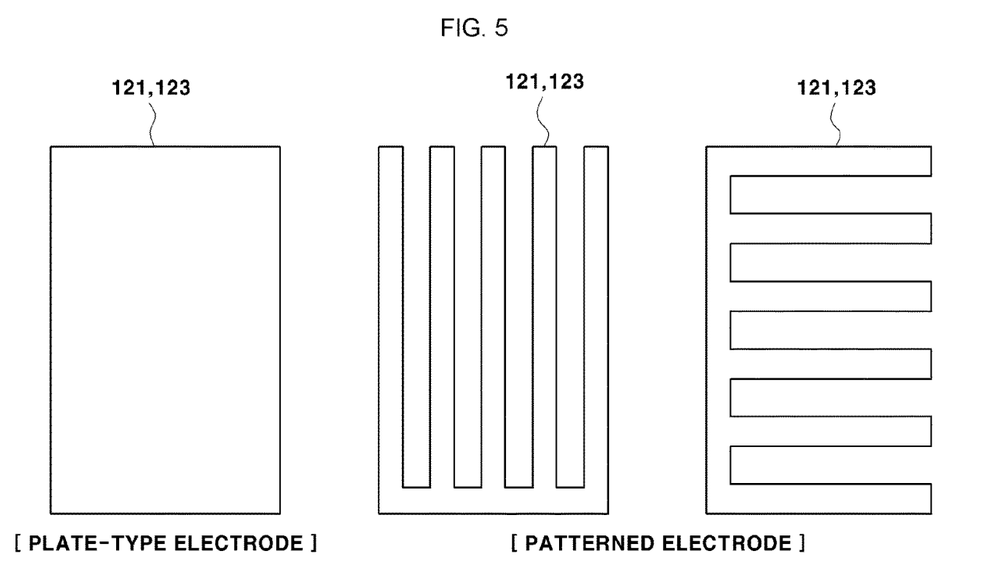
FIG. 5 is view exemplarily illustrating electrodes having various shapes in the particulate matter sensor in accordance with the form of the present disclosure.

FIG. 5 is view exemplarily illustrating electrodes having various shapes which are applicable to the sensing unit 120 of the particulate matter sensor 100 in accordance with the form of the present disclosure. As exemplarily shown in FIG. 5, a plate-type electrode manufactured as a thin sheet having a predetermined thickness may be used or, in order to reduce the amount of an electrode material consumed, a patterned electrode having a predetermined pattern may be used.

If a patterned electrode is used as the first electrode 121 and the second electrode 123, the first electrode 121 and the second electrode 123 are manufactured so as to have the same shape.

Further, the porous layer 124 may be configured so as to pass exhaust gas through open pore structures and to collect and accumulate particulate matter included in the exhaust gas on the inner surface of the porous layer 124.

In such a state in which the particulate matter is collected and accumulated in the porous layer 124, signal change between the first electrode 121 and the second electrode 123 occurs, a known external circuit reads the signal change and, thus, the amount of the accumulated particulate matter is measured (a capacitive type or resistive type).

In this variation of the present disclosure, the porous layer 124 of the sensing unit 120 may have a porous structure which is similar to a DPF and, more particularly, have a porous structure which may collect particulate matter without application of bias voltage.

Figure 6:
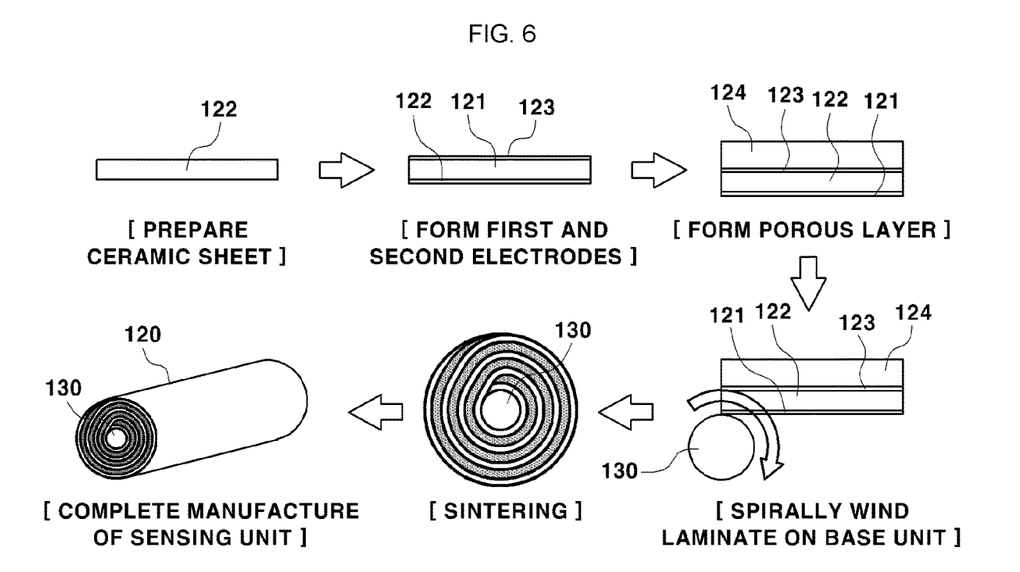
FIG. 6 is view exemplarily illustrating a method of manufacturing a sensing unit of a particulate matter sensor in accordance with one form of the present disclosure.

FIG. 6 is view exemplarily illustrating a method of manufacturing a sensing unit 120 of a particulate matter sensor 100 in accordance with one form of the present disclosure. As exemplarily shown in FIG. 6, a ceramic sheet having a designated thickness may be used as a substrate 122, and a first electrode 121 and a second electrode 123 are stacked on one surface and the other surface of the ceramic sheet serving as the substrate 122 through screen printing.

Thereafter, a porous layer 124 including a binder is stacked on the second electrode 123 through screen printing, and a laminate formed by sequentially stacking the first electrode 121, the substrate 122, the second electrode 123 and the porous layer 124 is spirally wound on a base unit 130 so as to surround the base unit 130, thus forming the sensing unit 120 having a cylindrical shape.

Here, the laminate is spirally wound on the base unit 130 such that the first electrode 121 may be bonded to the outer circumferential surface of the base unit 130 and thereafter, when a sintering process is carried out at a predetermine temperature, manufacture of the sensing unit 120 of the particulate matter sensor 100 may be completed.

The porous layer 124 is stacked on the second electrode 123 through screen printing, as described above, and stacking of a layer having a porous structure on a specific surface through a screen printing process is a known method which is industrially applicable and a detailed description thereof will thus be omitted.

In the present disclosure, the porous layer 124 may be formed of a ceramic material, the ceramic material of the porous layer 124 may be similar to or the same as the material of the substrate 122, and the porous layer 124 formed of a ceramic material may be stacked on the second electrode 123 through the screen printing process.

Porosity of the porous layer 124 may be adjusted by adding a porogen. Specifically, a ceramic slurry is manufactured by mixing alumina ($Al_2O_3$) powder and a binder (for example, vinyl chloride, vinylidene chloride, methyl methacryl or methyl methacrylate).

Thereafter, the ceramic slurry is applied to the second electrode 124 through the screen printing process and, for the purpose of molding and plasticity, the laminate is heated to a predetermined temperature (for example, 200° C.) at a predetermined pressure (for example, 15 MPa) so that the binder is deformed, and is then sintered at a high temperature (for example, 1,000° C.) for 1 hour, thereby manufacturing the porous layer 124.

A particulate matter sensor 100 in accordance with another variation of the present disclosure may further include a heater which heats a porous layer 124 of a sensing unit 120 so as to remove particulate matter and to regenerate the porous layer 124, and a temperature sensor which detects the temperature of the sensing unit 120.

Figure 7A:
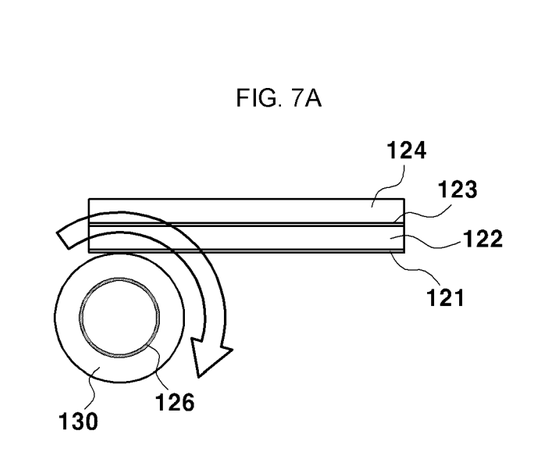
FIGS. 7A and 7B are views exemplarily illustrating a method of manufacturing a sensing unit, including a heater and a temperature sensor, of a particulate matter sensor in accordance with another variation of the present disclosure.

In the particulate matter sensor 100 in accordance with this form of the present disclosure, a heater and a temperature sensor 126 may be formed directly in and on the base unit 130, as exemplarily shown in FIG. 7A. Here, a known method for forming a heater and a temperature sensor at a specific region of a particulate matter sensor is applicable.

Figure 7B:
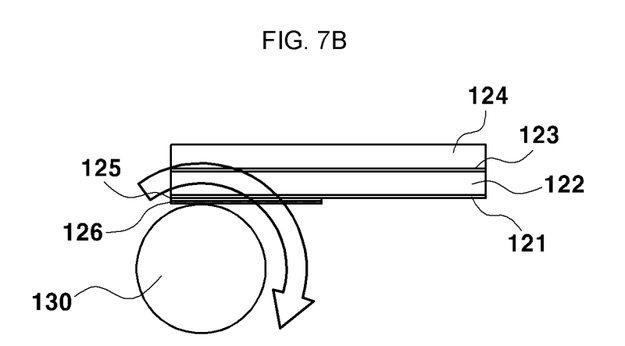

Otherwise, a heater and a temperature sensor 126 may be interposed between the base unit 130 and a laminate, as exemplarily shown in FIG. 7B.

The heater and the temperature sensor 126 may be also wound on the base unit 130.

For this purpose, an electrically insulating sheet 125, for example, a ceramic sheet, is stacked on the surface of a first electrode 121 stacked on the base unit 130, the heater and the temperature sensor 126 are stacked on the ceramic sheet 125, and the laminate is spirally wound on the base unit 130 such that the heater and the temperature sensor 126 are bonded to the base unit 130.

After such formation of the heater and the temperature sensor 126, in order to connect the heater and the temperature sensor 126 to a circuit (not shown) to operate the heater and the temperature sensor 126, a terminal (not shown) may be installed at a predetermined region of the heater and the temperature sensor 126 and the circuit located at the outside of the sensing unit 120 may be conductively connected to the terminal through wiring.

Further, terminals are installed at predetermined regions of the first electrode 121 and the second electrode 123 and a circuit to read a signal is conductively connected to the terminals connected to the electrodes 121 and 123 through wiring.

As is apparent from the above description, in a particulate matter sensor in accordance with the present disclosure, since a sensing unit is formed by spirally winding electrodes and a porous layer on a base unit so as to surround the base unit, a distance between the electrodes may be reduced, an area of measurement electrodes may be increased and, thus, enhancement in measurement accuracy and reliability, and enhancement in sensitivity may be achieved.

Further, sensitivity of the particulate matter sensor may be easily adjusted by controlling a thickness of the porous layer, an axial length of the sensing unit (a length of the cylindrical-shaped sensing unit), a diameter of the sensing unit, etc., and cost reduction and improvement in ease of mass production may be achieved.

Moreover, the sensing unit is manufactured so as to form a cylindrical shape around the base unit and, thus, influence of a sensor mounting direction on sensitivity of the particulate matter sensor may be removed.

The description is provided in detail with reference to preferred forms. However, it will be appreciated by those skilled in the art that changes may be made in these forms without departing from the principles and spirit of the present disclosure, the scope of which is defined in the appended claims and their equivalents.

What is claimed is:

1. A particulate matter sensor comprising:
   a housing provided with an inlet and an outlet configured so that exhaust gas introduced into the housing through the inlet passes through an inner space of the housing and is then discharged to a location outside of the housing through the outlet; and
   a sensing unit installed within the inner space of the housing and configured to pass the exhaust gas,
   wherein the sensing unit includes a laminate including an electrically insulating substrate, a first electrode provided on a first surface of the electrically insulating substrate, a second electrode provided on a second surface of the electrically insulating substrate, and a porous layer stacked on one of the first electrode and the second electrode and having a structure to pass the exhaust gas, and the laminate is spirally wound on a base unit.

2. The particulate matter sensor of claim 1, wherein the base unit is provided as a rod installed to be extended in an axial direction within the inner space of the housing, and the sensing unit is combined with the base unit at a position between the inlet and the outlet so that particulate matter is collected and accumulated in the porous layer passing the exhaust gas.

3. The particulate matter sensor of claim 1, wherein the housing includes:
   a cylindrical part provided with the sensing unit installed in an inner space thereof; and
   a diameter reduction part having a gradually reduced diameter and formed at one axial side of the cylindrical part,
   wherein the inlet is formed at the cylindrical part and the outlet is formed at the diameter reduction part.

4. The particulate matter sensor of claim 3, wherein the inlet includes a plurality of holes arranged at the cylindrical part at designated intervals in a circumferential direction of the cylindrical part.

5. The particulate matter sensor of claim 3, wherein the diameter reduction part has a conical shape, and the outlet is formed at one end of the conical diameter reduction part.

6. The particulate matter sensor of claim 1, wherein the sensing unit is configured such that the first electrode serves as the innermost layer bonded to an outer circumferential surface of the base unit, and the first electrode, the substrate, the second electrode and the porous layer are repeatedly sequentially stacked on the base unit in the outward direction.

7. The particulate matter sensor of claim 1, wherein a thickness of the porous layer corresponding to a distance between the first electrode and the second electrode is 20-50 μm.

8. The particulate matter sensor of claim 1, further comprising:
   a heater configured to heat the sensing unit including the porous layer so as to remove particulate matter and to regenerate the porous layer; and
   a temperature sensor configured to detect a temperature of the sensing unit,
   wherein the heater and the temperature sensor are provided at the base unit.

9. The particulate matter sensor of claim 1, further comprising:
   a heater configured to heat the sensing unit including the porous layer so as to remove particulate matter and to regenerate the porous layer; and
   a temperature sensor configured to detect a temperature of the sensing unit,
   wherein the heater and the temperature sensor together with the laminate are wound on the base unit.

* * * * *